United States Patent
Campbell et al.

(10) Patent No.: US 8,207,380 B2
(45) Date of Patent: Jun. 26, 2012

(54) ALKYLATED HYDROXYAROMATIC COMPOUND SUBSTANTIALLY FREE OF ENDOCRINE DISRUPTIVE CHEMICALS AND METHOD OF MAKING THE SAME

(75) Inventors: Curt B. Campbell, Hercules, CA (US); James J. Harrison, Novato, CA (US)

(73) Assignee: Chevron Oronite LLC, San Ramon, CA (US)

( * ) Notice: Subject to any disclaimer, the term of this patent is extended or adjusted under 35 U.S.C. 154(b) by 0 days.

(21) Appl. No.: 11/741,687

(22) Filed: Apr. 27, 2007

(65) Prior Publication Data

US 2008/0269351 A1    Oct. 30, 2008

(51) Int. Cl.
*C07C 37/00* (2006.01)
*C07C 15/067* (2006.01)
*A61K 31/05* (2006.01)

(52) U.S. Cl. ........ 568/793; 568/788; 568/785; 568/790; 568/792; 568/766; 585/446; 514/731

(58) Field of Classification Search .......... 568/716, 568/766, 790, 792
See application file for complete search history.

(56) References Cited

U.S. PATENT DOCUMENTS

| | | | |
|---|---|---|---|
| 4,475,001 A | 10/1984 | Leston | |
| 4,643,838 A | 2/1987 | Liston et al. | |
| 4,873,025 A | 10/1989 | Bolsman | |
| 4,912,264 A | 3/1990 | Takeshita et al. | |
| 4,973,764 A | 11/1990 | Oswald et al. | |
| 5,663,457 A | 9/1997 | Kolp | |
| 5,922,922 A | 7/1999 | Harris et al. | |
| 6,191,317 B1 | 2/2001 | Su | |
| 6,670,513 B1 * | 12/2003 | Campbell et al. | 568/793 |
| 6,765,106 B2 | 7/2004 | Fenouil et al. | |
| 7,022,763 B2 | 4/2006 | Matsugi et al. | |
| 7,041,864 B2 | 5/2006 | Fong et al. | |
| 7,087,777 B2 | 8/2006 | Fenouil et al. | |
| 7,157,613 B2 | 1/2007 | Arnoldy | |

FOREIGN PATENT DOCUMENTS

| | | | |
|---|---|---|---|
| CS | 226 912 | | 4/1984 |
| CS | 226912 | * | 4/1984 |
| EP | 1 548 089 | | 6/2005 |
| EP | 1 760 135 | | 3/2007 |

OTHER PUBLICATIONS

International Search Report and Written Opinion issued in counterpart Singapore Patent Application No. 200803075-1.
International Search Report issued in counterpart European Patent Application No. 08251077.7.
Product brochure from Rohde and Haas or Amberlyst® 36 sulfonic acid.

* cited by examiner

*Primary Examiner* — Yate K Cutliff
(74) *Attorney, Agent, or Firm* — Josetta I. Jones; Michael Carmen

(57) ABSTRACT

An alkylated hydroxyaromatic compound prepared by reacting at least one hydroxyaromatic compound with a branched olefinic oligomer having from about 20 to about 80 carbon atoms in the presence of a acid catalyst. The alkylated hydroxyaromatic compound has been determined to be substantially free of endocrine disruptive chemicals when the effects were quantified on pubertal development and thyroid function in the intact juvenile female rat.

5 Claims, 1 Drawing Sheet

Dose Response Plot

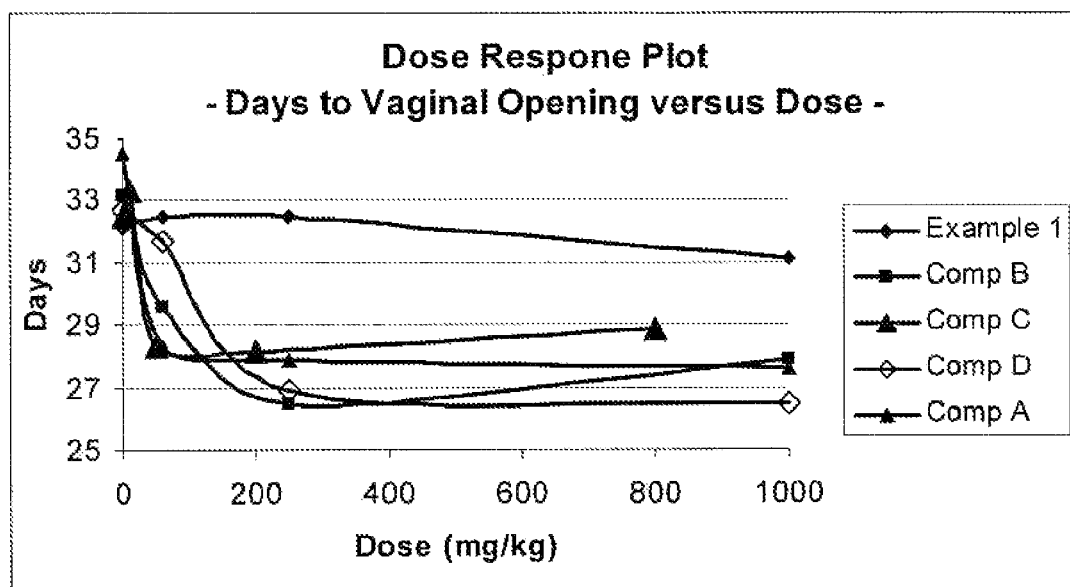
Dose Response Plot

ALKYLATED HYDROXYAROMATIC COMPOUND SUBSTANTIALLY FREE OF ENDOCRINE DISRUPTIVE CHEMICALS AND METHOD OF MAKING THE SAME

FIELD OF THE INVENTION

The present invention is directed to an alkylated hydroxyaromatic compound and a method of making the alkylated hydroxyaromatic compound. The compound is prepared by reacting at least one hydroxyaromatic compound with a propylene oligomer in the presence of an acid catalyst. The resulting branched chain alkylated hydroxyaromatic compound has been determined to be substantially free of endocrine disruptive chemicals when the effects were quantified on pubertal development and thyroid function in the intact juvenile female rat.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), hydrogen fluoride, solid acid catalysts such as acidic sulfonic acid ion exchange resins, for example Amberlysts®, solid acid clays and acidic zeolitic materials. Alkylation with lower molecular weight olefins, such as propylene, can be carried out in the liquid or vapor phase. For alkylations with higher olefins, such as $C_{16+}$ olefins, the alkylations are done in the liquid phase.

There is increasing evidence that certain synthetic and natural chemicals may act as agonists or antagonists to estrogens or androgens and may interfere in multiple ways with the action of thyroid hormones; such compounds can be called endocrine disruptors. For example, endocrine disruptors can mimic or block chemicals naturally found in the body, thereby altering the body's ability to produce hormones, interfering with the ways hormones travel through the body, and altering the concentration hormones reaching hormone receptors. Endocrine disruptors and natural estrogens share a common mechanism of action. In normal cases, estrogenic activity is produced by binding natural estrogen to an estrogen receptor (ER) within the nucleus of the cell, followed by transcriptional activation of these occupied ERs. When endocrine disruptors are present, normal estrogenic activity is supplanted when endocrine disruptors bind an ER, causing transcriptional activation of the ER even though no natural estrogen is present. Similarly, antiestrogenic activity is produced by endocrine disruptors which bind to ERs but which do not subsequently activate the occupied ER as well as natural estrogen. Finally, selective estrogen receptor modulators (SERMs) bind to ERs, but subsequently activate cellular responses that differ from those activated by the natural estrogens. In general, all but a very small number of molecules that bind to ERs produce some activation of the receptors, as either estrogens or as SERMs.

Examples of suspected endocrine disruptors may include, for example: Dioxin, Polychlorinated biphenyls (PCBs), Polybromated biphenyls (PBBs), Hexachlorobenzene (HCB), Pentachlorophenol (PCP), 2,4,5-Trichlorophenoxy acetic acid (2,4,5-T), 2,4-Dichlorophenoxyacetic acid (2,4-D), alkylphenols such as Nonylphenol or Octylphenol, Bisphenol A, Di-2-ethylhexyl phthalate (DEHP), butylbenzyl phthalate (BBP), Di-n-butyl phthalate (DBP), Dicylclohexyl phthalate (DCHP), Diethyl phthalate (DEP), Benzo (a) pyrene, 2,4-Dichlorophenol (2,4-DPC), Di(2-ethylhexyl)adipate, Benzophenone, P-Nitrotoluene, 4-Nitrotoluene, Octachlorostyrene, Di-n-pentyl phthalate (DPP), Dihexyl phthalate (DHP), Dipropyl phthalate (DprP), Styrene dimers and trimers, N-Butyl benzene, Estradiol, Diethylhexyl adipate (DEHA), trans-chlorodane, cis-chlorodane, p-(1,1,3,3-Tetramethylbutyl)phenol (TMBP), and (2,4,-Dichlorophenoxy) acetic acid (2,4-PA).

Alkylphenols and products produced by them have come under increased scrutiny due to their association as potential endocrine disruptive components, which is namely due to the weak estrogenic activity of base alkylphenol as well as degradation intermediates of the alkylphenols products. Alkylphenols commercially are used in herbicides, gasoline additives, dyestuffs, polymer additives, surfactants, lubricating oil additives and antioxidants. In the recent years, alkylphenol alkoxylates, such as ethoxylated nonylphenol, have been criticized for having poor biodegradability, high aquatic toxicity of the by-products of the biodegradation of the phenol portion, and there is an increasing concern that these chemicals may act as endocrine disruptors. Some studies have shown that there are links between alkylphenols and declining sperm count in human males and there is evidence that alkylphenols may harmfully disrupt the activity of human estrogen and androgen receptors.

Concern over the environmental and health impact of alkoxylated alkylphenols has led to governmental restriction on the use of these surfactants in Europe, as well as voluntary industrial restrictions in the United States. Many industries have attempted to replace these preferred alkoxylated alkylphenol surfactants with alkoxylated linear and branched alkyl primary and secondary alcohols, but have encountered problems with odor, performance, formulating, and increased costs. The odor and some of the performance difficulties of the alkoxylated alkyl alcohols are related to the residual free alcohol, which is the portion of the reactant alcohol that does not react with alkylene oxide during the alkoxylation step.

DESCRIPTION OF THE RELATED ART

Bolsman, U.S. Pat. No. 4,873,025 discloses alkylxylene sulfonate composition prepared by alkylating a para-xylene reactant (or mixture of xylene isomers containing at least about 25 wt % para-xylene), sulfonating the resulting alkylate, and, optionally, converting the product alkylxylene sulfonic acid(s) into the salts. The alkylation may be carried out in a manner known for analogous compounds, e.g., by a Friedel-Crafts reactions using alkyl halide, alkanol, or alkene reactant, in the presence of a Lewis acid catalyst. Preferably the catalyst is hydrogen fluouride or an activated clay.

Arnoldy, U.S. Pat. No. 7,157,613 discloses a process for producing branched olefins from a mixed linear olefin/paraffin isomerisation feed comprising linear olefins.

Fenouil et al., U.S. Pat. No. 7,087,777 disclose a process for preparing branched olefins comprising 0.5% or less quaternary aliphatic carbon atoms, which process comprises dehydrogenating an isoparaffinic composition over a suitable catalyst which isoparaffinic composition comprises paraffins having a carbon number in the range of from 7 to 35, of which paraffins at least a portion of the molecules is branched, the average number of branches per paraffin molecule being at least 0.7 and the branching comprising methyl and optionally ethyl branches, and which isoparaffinic composition may be obtained by hydrocracking and hydroisomerization of a paraffinic wax.

Fong et al., U.S. Pat. No. 7,041,864, disclose a method for producing linear and/or branched unsaturated product hydrocarbons used ring opening cross-metathesis.

Matsugi et al., U.S. Pat. No. 7,022,763 disclose a branched olefin copolymer and a method for making said copolymer. The branched moiety is formed by radical polymerization reaction or anion polymerization reaction.

Fenouil et al., U.S. Pat. No. 6,765,106 disclose a process for preparing branched olefins comprising 0.5% or less quaternary aliphatic carbon atoms, which process comprises dehydrogenating an isoparaffinic composition over a suitable catalyst which isoparaffinic composition comprises paraffins having a carbon number in the range of from 7 to 35, of which paraffins at least a portion of the molecules is branched, the average number of branches per paraffin molecule being at least 0.7 and the branching comprising methyl and optionally ethyl branches, and which isoparaffinic composition may be obtained by hydrocracking and hydroisomerization of a paraffinic wax.

Harris et al., U.S. Pat. No. 5,922,922 disclose an alkylated aromatic hydrocarbon that is produced having the following properties: (a) less than 40 wt % of the alkylated aromatic hydrocarbon is 2-aryl; and (b) at least 20 wt. % of the alkylated aromatic hydrocarbon is a monoaklylate.

Oswald et al., U.S. Pat. No. 4,973,764 disclose a process for alkylating phenols wherein phenols are alkylated with the olefin component of a thermally cracked sulfur containing petroleum distillate derived from residua in the presence of an acid catalyst to provide monoalkylphenols which have an average of less than two alkyl branches in the said alkyl group.

Takeshita et al., U.S. Pat. No. 4,912,264 disclose a process for producing hydroxyl-containing alkylated aromatic compounds by the liquid phase reaction of an aromatic compound having at least one hydroxyl group with an alkylating agent in the presence of a heteropoly acid and water.

Leston, U.S. Pat. No. 4,475,001 discloses a process for alkylating phenolic compounds to produce ortho-or para-monoalkylated phenols or 2,4-or 2,6-dialkylated phenols.

BRIEF DESCRIPTION OF THE DRAWINGS

FIG. 1 is a dose response plot to assess pubertal development in juvenile female rats. The data in FIG. 1 demonstrate sensitivity of the assay to differentiate among the compounds tested in capability to disrupt endocrine function as measured by sexual maturation.

SUMMARY OF THE INVENTION

In one embodiment, the present invention is directed to an alkylated hydroxyaromatic compound prepared by a process comprising reacting at least one hydroxyaromatic compound with a branched olefinic propylene oligomer having from about 20 to about 80 carbon atoms in the presence of an acid catalyst, to provide an alkylated hydroxyaromatic compound wherein the benzylic carbon attached to the hydroxyaromatic ring is substituted with one alkyl group having 1 to 5 carbon atoms and a second alkyl group of at least 18 carbon atoms having an average of one branch every 2 carbon atoms wherein each branch contains 1 to 2 carbon atoms.

In another embodiment, the present invention is directed to a process for alkylating an hydroxyaromatic compound comprising reacting at least one hydroxyaromatic compound with a branched olefinic propylene oligomer having from about 20 to about 80 carbon atoms in the presence of a acid catalyst, wherein the resulting product comprises an alkylated hydroxyaromatic compound having the following structure:

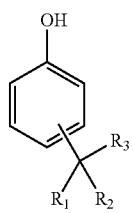

wherein $R_1$ is a branched alkyl group of at least 18 carbon atoms having an average of at least one branch every 2 carbon atoms wherein each branch contains 1 to 2 carbon atoms, $R_2$ is an alkyl group having 1 to 5 carbon atoms, and $R_3$ is either hydrogen or an alkyl group.

In another embodiment, the present invention is directed to a lubricating oil composition comprising:
(a) a major amount of an oil of lubricating viscosity; and
(b) an alkylated hydroxyaromatic compound prepared by a process comprising: reacting at least one hydroxyaromatic compound with a branched olefinic propylene oligomer having from about 20 to about 80 carbon atoms in the presence of a acid catalyst, wherein the resulting product comprises an alkylated hydroxyaromatic compound having the following structure:

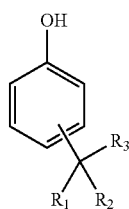

wherein $R_1$ is a branched alkyl group of at least 18 carbon atoms having an average of at least one branch every 2 carbon atoms wherein each branch contains 1 to 2 carbon atoms, $R_2$ is an alkyl group having 1 to 5 carbon atoms, and $R_3$ is either hydrogen or an alkyl group.

DETAILED DESCRIPTION OF THE INVENTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.
Definitions Olefins—The term "olefins" refers to a class of unsaturated aliphatic hydrocarbons having one or more carbon-carbon double bonds, obtained by a number of processes. Those containing one double bond are called mono-alkenes, and those with two double bonds are called dienes, alkyldienes, or diolefins. Alpha olefins are particularly reactive because the double bond is between the first and second carbons. Examples are 1-octene and 1-octadecene, which are used as the starting point for medium-biodegradable surfactants. Linear and branched olefins are also included in the definition of olefins.

Partially Branched Linear Olefins—The term "partially branched linear olefins" refers to a class of linear olefins comprising less than one alkyl branch per straight chain containing the double bond, wherein the alkyl branch may be a methyl group or higher. Partially branched linear olefins may also contain double-bond isomerized olefin.

Branched Olefins—The term "branched olefins" refers to a class of olefins comprising one or more alkyl branches per linear straight chain containing the double bond, wherein the alkyl branch may be a methyl group or higher.

Non-Hydroxyl Containing Aromatic Compounds—The term "non-hydroxyl containing aromatic compounds" refers to aromatic compounds that do not have any hydroxyl groups either on the aromatic ring or on any substituent group(s).

Unsubstituted Aromatic Compounds—The term "unsubstituted compounds" refers to aromatic compounds that do not have any substituents attached to the aromatic ring(s). These compounds may be monocyclic, bicyclic or polycyclic. Examples of such compounds include, but are not limited to, benzene, naphthalene and the like.

Monosubstituted Aromatic Compounds—The term "monosubstituted compounds" refers to aromatic compounds that have one substituent attached to the aromatic ring. These compounds may be monocyclic, bicyclic or polycyclic. Examples of such compounds include, but are not limited to, aromatic compounds with one of the following substituents: —OR, —R, —X, —NH$_2$, —NHR or —NR$_2$ and the like, wherein R is an alkyl group and X is a halide.

Disubstituted Aromatic Compounds—The term "disubstituted compounds" refers to aromatic compounds that have two substituents attached to the aromatic ring(s). The aromatic compounds may be monocyclic, bicyclic or polycyclic. Examples of such compounds include, but are not limited to, aromatic compounds with two substituents selected from the following: —OR, —R, —X, —NH$_2$, —NHR or —NR$_2$ and the like, wherein R is an alkyl group and X is a halide.

Hydroxyaromatic Compound

At least one hydroxyaromatic compound or a mixture of hydroxyaromatic compounds may be used for the alkylation reaction in the present invention. The hydroxyaromatic compounds that may be alkylated in accordance with the process of the present invention include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like. The preferred hydroxyaromatic compound is phenol.

Sources of Hydroxyaromatic Compound

The at least one hydroxyaromatic compound or the mixture of hydroxyaromatic compounds employed in the present invention is prepared by methods that are well known in the art.

Olefins

Sources of Olefins

The olefins employed in this invention are branched chain olefins derived from the polymerization of propylene. The olefin may be a mixture of branched olefins.

The olefins may also be substituted with other functional groups, such as hydroxy groups, carboxylic acid groups, heteroatoms, and the like, provided that such groups do not react with the acidic ionic liquid catalyst.

The mixture of olefins is selected from propylene oligomers with carbon numbers ranging from about 20 carbon atoms to about 80 carbon atoms. Preferably, the mixture of olefins is selected from propylene oligomers with carbon numbers ranging from about 20 to about 60 carbon atoms, more preferred from about 20 to about 40 carbon atoms.

In one embodiment, the branched olefin is attached to the hydroxyaromatic compound such that the benzylic carbon atom attached to the hydroxaromatic ring is substituted with one alkyl group having 1 to 5 carbon atoms and a second alkyl group of at least 18 carbon atoms having an average of one branch every 2 carbon atoms wherein each branch contains 1 to 2 carbon atoms.

Acid Catalyst

Typically, the alkylated aromatic compound may be prepared using acid catalysts (Bronsted or Lewis acids).

Preferably, the acid catalyst comprises hydrochloric acid, hydrofuoric acid, hydrobromic acid, sulfuric acid, perchloric acid, trifluoromethane sulfonic acid, fluorosulfonic acid, Amberlyst® 36 sulfonic acid, which may be purchased from Rohm and Haas, nitric acid or the like.

The alkylation process may be carried out in a batch or continuous process. The acid catalyst may be recycled or regenerated when used in a batch process or a continuous process.

The acid catalyst may be regenerated after it becomes deactivated (i.e., the catalyst has lost all or some portion of its catalytic activity). Methods that are well known in the art may be used to regenerate the deactivated hydrofluoric acid catalyst.

Preparation of Olefinic Oligomer

The olefinic oligomers employed in the present invention are synthesized by oligomerizing propylene in the presence of an acid catalyst. Preferably, the olefinic oligomer has a carbon range of from about 20 to about 80.

The olefin oligomer may be prepared by reacting the propylene monomer with the acidic ionic liquid catalyst, as described herein, in a continuous, batch or semi-batch reaction process at from about −20° C. to about 100° C. and a pressure of atmospheric pressure to about 1000 psig. These process conditions are not limiting. Optimization of process conditions in the oligomerization of the olefin is within the scope of this invention.

Process for Preparing Alkylated Hydroxyaromatic Compound

In one embodiment of the present invention, the alkylation process is carried out by charging a hydrocarbon feed comprising an hydroxyaromatic compound or a mixture of hydroxyaromatic compounds, a mixture of olefin compounds (i.e., polypropylene oligomers) and an acid catalyst to a reaction zone in which agitation is maintained. The resulting mixture is held in the alkylation zone under alkylation conditions for a time sufficient to allow substantial conversion (i.e., at least 70 mole % of the olefin has reacted) of the olefin to hydroxyaromatic alkylate. After the desired time, the reaction mixture is removed from the alkylation zone and fed to a liquid-liquid separator to allow hydrocarbon products to separate from the acid catalyst which may be recycled to the reactor in a closed loop cycle. The hydrocarbon product is further treated to remove excess un-reacted hydroxyaromatic compounds and optionally olefinic compounds from the desired alkylate product. The excess hydroxyaromatic compounds can also be recycled to the reactor.

Many types of reactor configurations may be used for the reactor zone. These include, but are not limited to, batch and continuous stirred tank reactors, reactor riser configurations, ebulating or fixed bed reactors, and other reactor configurations that are well known in the art. Many such reactors are known to those skilled in the art and are suitable for the alkylation reaction. In batch or semi-batch reactors, agitation is critical for the alkylation reaction and can be provided by rotating impellers, with or without baffles, static mixers, kinetic mixing in risers, or any other agitation devices that are well known in the art.

The alkylation process may be carried out at temperatures from about 0° C. to about 200° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the olefin to alkylate product. The time required is from about 30 seconds to about 300 minutes. A more precise residence time may be determined by those skilled in the art using batch stirred tank reactors to measure the kinetics of the alkylation process.

The at least one hydroxyaromatic compound or mixture of hydroxyaromatic compounds and the mixture of olefins may be injected separately into the reaction zone or may be mixed prior to injection. Both single and multiple reaction zones may be used with the injection of the hydroxyaromatic compounds and the mixture of olefins into one, several, or all reaction zones. The reaction zones need not be maintained at the same process conditions.

The hydrocarbon feed for the alkylation process may comprise a mixture of hydroxyaromatic compounds and a mixture olefins in which the molar ratio of hydroxyaromatic compounds to olefins is from about 0.5:1 to about 50:1 or more. In the case where the molar ratio of hydroxyaromatic compounds to olefin is >1.0 there is an excess amount of hydroxyaromatic compounds present. Preferably an excess of hydroxyaromatic compounds is used to increase reaction rate and improve product selectivity. When excess hydroxyaromatic compounds are used, the excess un-reacted hydroxyaromatic in the reactor effluent can be separated, e.g. by distillation, and recycled to the reactor.

One embodiment of the alkylation process is a continuous process with closed loop catalyst recycle. A hydrocarbon feed comprising hydroxyaromatic compound(s) or a mixture of hydroxyaromatic compounds and a mixture of olefin(s) is charged continuously to a reactor. Alternatively, the hydroxyaromatic compound(s) and mixture of olefin(s) may be charged by separately. At the beginning of the process, an amount of fresh acid catalyst is charged through to the reactor. The hydrocarbon feed and acidic ionic liquid catalyst are maintained in the reactor with agitation under alkylation process conditions for a sufficient time in order for a substantial amount of the mixture of olefins in the feed charge to react and form an hydroxyaromatic alkylate compound. Pressure in the reactor is maintained by a backpressure valve. The effluent from the reactor is passed through a backpressure valve to the separator. In the separator, the immiscible hydrocarbon and acid catalyst separate into two phases. As the acid catalyst is more dense than the hydrocarbon phase, the acid catalyst settles to the bottom of the separator. When a sufficient volume of acid catalyst is available to fill line and the bottom of the separator, the flow of fresh catalyst is stopped and "used" or "recycled" catalyst is returned to the reactor from the separator. In this embodiment, the major portion of this process is thus operated under conditions of catalyst recycle, under which no fresh catalyst is added or only a small amount of make-up catalyst is added. The hydrocarbon product stream containing the hydroxyaromatic alkylate compound and excess un-reacted hydroxyaromatic is charged to a product separation section. In product separation, excess hydroxyaromatic compounds are distilled off and returned to the reactor, leaving an alkylated hydroxyaromatic compound.

Alkylated Hydroxyaromatic Compound

The resulting product is an alkylated hydroxyaromatic compound having the following structure:

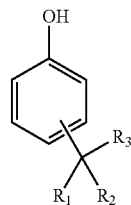

wherein $R_1$ is a branched alkyl group of at least 18 carbon atoms having an average of at least one branch every 2 carbon atoms wherein each branch contains 1 to 2 carbon atoms, $R_2$ is an alkyl group having 1 to 5 carbon atoms, and $R_3$ is either hydrogen or an alkyl group.

Preferably, the resulting product will be a mixture of ortho and para isomers. Typically, the product will contain about 1 to 99% ortho isomer and 99 to 1% para isomer, and preferably, about 5 to 70% ortho and 95 to 30% para isomer.

Other embodiments will be obvious to those skilled in the art.

The following examples are presented to illustrate specific embodiments of this invention and are not to be construed in any way as limiting the scope of the invention.

EXAMPLES

Example 1—Preparation of Propylene Oligomer Alkylphenol

A 2-liter glass, 4-neck, round bottom flask fitted with a mechanical stirrer, water condenser, liquid addition funnel and thermometer was charged with 268.9 gm (2.86 moles) of phenol under a nitrogen atmosphere. The temperature of the reaction was raised to 130° C. with agitation and approximately 6.7 gm of trifluoromethane sulfonic acid was added dropwise via syringe (the reaction mixture turned an orange color) followed immediately by 787 gm (approximately 0.95 moles) of polypropylene oligomer via an the addition funnel. The reaction mixture was held at 130° C. for 2 hours and then cooled to room temperature, diluted with 1 liter of hexane and washed with aqueous saturated sodium bicarbonate solution. The organic layer was dried over anhydrous magnesium sulfate, gravity filtered and the solvent removed under vacuum with to afford 806 gm of a brown oil. A portion (775 gm) of this brown oil was fractionally vacuum distilled (10"×2" unpacked Vigreux column at 1.0 Torr and temperature programmed from 151 to 204° C.) to remove any remaining unreacted phenol and yielded 725 gm of a second brown oil. A portion of this second brown oil (575 gm) was fractionally vacuum distilled a second time (10"×2" unpacked Vigreux column at 0.3 Torr and temperature programmed from 193 to 240° C.) to remove any $C_2$-$C_{18}$ alkylphenol and afforded the purified propylene oligomer alkylphenol: 1H NMR, 0.3-2.0 ppm (aliphatic C—H), 4-5 ppm (O—H) and 6.6-7.6 ppm (aromatic C—H); IR 745 cm−1 (ortho-alkylphenol), 825 cm−1 (para-alkylphenol); HPLC (5 cm×4.6 cm 5μ C8 Column, 78:22 methanol:water 10 minutes then 85/15 100% Methanol for 35 minutes at 1 ml/min, 2 microliter injection using a Fluorescence 225×313 em) showed 0.02 weight % $C_2$-$C_{18}$ alkylphenol present; Adsorption chromatography (Silica Gel SepPak®, hexane, then di-ethylether) showed the propylene oligomer alkylphenol to contain 70.0 weight % alkyphenol with the remainder being unreacted polypropylene oligomer.

Comparative Example A—Purified Propylene Tetramer Alkylphenol Calcium Salt

Branched dodecyl phenol calcium salt was prepared from the alkylation of phenol with a mixture of branched chain $C_{10}$-$C_{15}$ olefin derived primarily from propylene tetramer and the resulting alkylphenol had the following carbon distribution:

| Carbon Number | Wt % |
|---|---|
| $\leq C_9$ | 0 |
| $C_{10,11}$ | 6.6 |
| $C_{12}$ | 82.7 |
| $C_{13+}$ | 10.7 |

To a 5 neck, 3 liter round bottom flask equipped with a mechanical stirrer, Dean Stark trap fitted with a condenser under an atmosphere of dry nitrogen was charged 607 gm (2.32 moles) of the above C12: branched alkylphenol followed by 500 gm of Chevron RLOP 100N oil. This mixture was heated to approximately 150° C. and maintained at this temperature overnight with stirring. The mixture was then cooled to approximately 20° C. using an ice bath and 48.8 gm (1.16 moles) of calcium hydride ($CaH_2$, 98% obtained from Aldrich Chemical Company) was added to the mixture in approximately 10 gram portions with stirring. The mixture was then heated to approximately 270° C. in approximately 1 hour and held at this temperature with stirring for 8 hours. The mixture was then cooled to 200° C. overnight and then raised the temperature to 280° C. and held there for 4 hours. The mixture was then cooled to 230° C. and maintained at this temperature overnight. The mixture was then cooled to approximately 150° C. and filtered through a sintered glass Buchner funnel containing Celite® filter aid (dried overnight at 120° C.) into a dry filter flask with the aid of vacuum over approximately 3.5 hours. The resulting light honey colored liquid contained 3.82% calcium. This reaction was repeated and the combined products were a honey colored liquid containing 3.82% calcium.

Comparative Example B—Propylene Pentamer Alkylphenol Calcium Salt

Branched pentadecylphenol calcium salt was prepared from the alkylation of phenol with a branched chain $C_{14}$-$C_{18}$ olefin derived primarily from propylene pentamer. To a 2-liter round bottom flask equipped with a mechanical stirred, Dean Stark trap fitted with a condenser under an atmosphere of dry nitrogen was charged with 705 gm (2.32 moles) of a $C_{15}$ branched alkylphenol followed by 500 gm of Chevron RLOP 100N oil. This mixture was cooled to approximately 13° C. using an ice bath and then 48.8 gm (1.16 moles) of calcium hydride (98% obtained from Aldrich Chemical Company) was added in approximately 10 gram portions with stirring. The reaction was then heated to 100° C. over 50 minutes and then heated to 200° C. for over 140 minutes and held at 200° C. for approximately 18 hours and then heated to 280° C. over 1 hour and held at 280° C. for 8.5 hours and then cooled to 230° C. and held at 230° C. for approximately 14 hours. The reaction was then cooled to 150° C. and filtered through a dry, hot (150° C.) 600 mL Buchner funnel containing a filter bed of Celite and maintained between 110° C. and 120° C. with the aid of a vacuum to afford a product containing 3.51 wt % calcium.

Comparative Example C—Propylene Tetramer Alkylphenol

Branched, principally, $C_{12}$ or branched dodecyl phenol, was prepared from the alkylation of phenol with a branched chain $C_{10}$-$C_{15}$ olefin derived from propylene tetramer and the resulting alkylphenol had the following carbon distribution:

| Carbon Number | Wt % |
|---|---|
| $\leq C_{10}$ | 1 |
| $C_{11}$ | 18 |
| $C_{12}$ | 59 |
| $C_{13}$ | 17 |
| $C_{14}$ | 4 |
| $\geq C_{15}$ | 1 |

Comparative Example D—Propylene Tetramer Dimer Alkylphenol

A glass, three-neck, round bottom flask fitted with a mechanical stirrer, water condenser and thermometer was charged with 896 gm (2.7 moles) of propylene tetramer dimer and 82.4 gm of Amberlyst® 36 sulfonic acid ion exchange resin. This mixture was heated to 90° C. with stirring and then 753 gm (8.0 moles) of phenol was charged to the reactor. The temperature of the 1.5 reaction was increased to 120° C. and held for 24 hours. The temperature of the reaction was then increased to 130° C. for 1.5 hours and then allowed to cool to room temperature. The reaction mixture was then filtered with the aid of vacuum through a glass fritted Buchner funnel. The resulting filtrate (1721 gm) was fractionally vacuum distilled (10"×2" Vigreux column, 10-50 Torr, temperature programmed from 111 to 180° C. to remove unreacted phenol and afforded 1079 gm a bottoms product. The above alkylation reaction was repeated and the combined distilled bottoms product (1721 gm) were fractionally vacuum distilled a second time (10"×2" Vigreux column, 1.0 Torr, temperature programmed from 100 to 195° C.) to remove any $C_2$-$C_{18}$ alkylphenol and afforded 675 gm of the purified propylene tetramer dimer alkylphenol: IR 745 cm−1 (ortho-alkylphenol), 825 cm−1 (para-alkylphenol); FIMS analysis showed the presence of $C_{10}$-$C_{31}$ alkylphenols; HPLC (5 cm×4.6 cm 5 μC8 Column, 78:22 methanol: water 10 minutes then 85/15 100% Methanol for 35 minutes at 1 ml/min, 2 microliter injection using a Fluorescence 225×313 em) showed 3.05 weight % $C_2$-$C_{18}$ alkylphenol present; Adsorption chromatography (Silica Gel SepPak®, hexane, then di-ethylether) showed the propylene tetramer dimer alkylphenol contained 88.0 weight % alkylphenol with the remainder being unreacted polypropylene tetramer dimer.

Assessment

Assessment of Pubertal Development in Juvenile Female CD® (Sprague-Dawley) Rats was carried out after exposure to the compounds of Example 1 and Comparative Examples A-D, administered by oral gavage. This assessment is a modified version of the toxicology screen referred to as the "female pubertal assay." This assay detects estrogenic and anti-estrogenic activity as well as perturbations to the hypothalamic-pituitary-gonadal/thyroidal axis during the course of twenty days of test substance administration. Effects are detected via changes to the timing of sexual maturation (age at vaginal opening), changes to organ weights, and age at first estrus. This assay is designed to be sensitive to endocrine endpoints, but is an apical design from the perspective that it cannot single out one particular endocrine-mediated mechanism.

It should be noted that the female pubertal assay is an apical assay that may detect chemicals with biological activity upon the hypothalamic-pituitary-gonadal/thyroidal axes. Chemicals what act directly upon the female gonads, such as those described as estrogen mimics, would also be detected in a simpler assay known as the uterotrophic assay. The uterotrophic assay is specific for estrogenicity. However, the female pubertal assay should detect both chemicals that act directly upon the female gonads as well as chemicals that act upon other components in these endocrine axes.

Briefly, the assay is conducted as follows. Suitable female rats, 21 days of age, within the weight range were weaned and randomized into four treatment groups. Each treatment group consisted of fifteen females. Dosage levels were determined and dose volumes were based on daily body weight. Animals were orally dosed with a test compound or the vehicle (Mazola® corn oil) beginning on day 22 and continuing through 41 days of age. A separate vehicle control group dosed with corn oil was run concurrently with each component. Clinical signs were observed twice daily during the experimental period with body weights recorded daily. Beginning with postnatal day "PND" PND 25, animals were examined for vaginal perforation. The day of complete vaginal perforation was identified as the age of vaginal opening, and body weight was recorded on that day. Daily vaginal smears to determine the stage of estrus were performed beginning on the day of vaginal perforation until necropsy. At necropsy on PND 42, females were euthanized and blood was collected from the vena cava for analysis of Thyroid Stimulating Hormone (TSH) and Thyrroxine ($T_4$). Uterine, ovary, liver, pituitary, kidney, thyroid and adrenal weights were collected. Body weights, body weight gains, organ weights (wet and blotted) luminal fluid weights, mean day of acquisition of vaginal perforation, mean age of first estrous and estrous cycle length was analyzed using statistical methods, such as by a parametric one-way analysis of variance, (ANOVA) to determine intergroup differences.

TABLE 1

Vaginal Opening and Body Weight of Treated Females

| Compound | Dose (mg/kg/day) | Days to Vaginal Opening | Body weight at Sexual Maturation |
|---|---|---|---|
| Example 1 | 0 | 32.1 | 111.4 |
| | 60 | 32.5 | 112.4 |
| | 250 | 32.5 | 112.2 |
| | 1000 | 31.1 | 103.4 |
| Comparative Example A | 0 | 34.5 | 105.9 |
| | 60 | 28.3 | 104.4 |
| | 250 | 27.9 | 96.0 |
| | 1000 | 27.6 | 74.6 |
| Comparative Example B | 0 | 33.2 | 110.9 |
| | 60 | 29.6 | 89.7 |
| | 250 | 26.5 | 75.2 |
| | 1000 | 27.9 | 77.4 |
| Comparative Example C | 0 | 32.5 | 111.9 |
| | 10 | 33.3 | 113.6 |
| | 50 | 28.3 | 85.4 |
| | 200 | 28.2 | 83.4 |
| | 800 | 28.9 | 73.9 |
| Comparative Example D | 0 | 32.7 | 109.7 |
| | 60 | 31.7 | 98.5 |
| | 250 | 26.9 | 73.9 |
| | 1000 | 26.5 | 71.9 |

The data in Table 1 demonstrate sensitivity of the assay to differentiate among the compounds in capability to disrupt endocrine function as measured by sexual maturation.

Example 1, even at very high dosages, showed no evidence of endocrine disruption as measured by a decrease in days to vaginal opening (See Table 1 and FIG. 1) or decrease in body weight at sexual maturation. (See Table 1). By comparison, Comparative Examples A, B, C and D showed evidence of endocrine disruption. In addition, the Comparative Examples A, B, C and D exhibited a decreasing trend in body weight, with a significant effect at high dose rates, similar decreasing trends were also noted for regarding the average postnatal day of vaginal opening. It should also be noted that potency does not vary greatly between the free alkylphenol and the calcium salt (See Comparative Examples A and C).

While the invention has been described in terms of various preferred embodiments, the skilled artisan will appreciate that various modifications, substitutions, omissions, and changes may be made without departing from the spirit thereof. Accordingly, it is intended that the scope of the invention be limited solely by the scope of the following claims, including equivalents thereof.

What is claimed is:

1. A process for alkylating an hydroxyaromatic compound comprising reacting at least one phenol compound with a branched olefinic propylene oligomer having from about 20 to about 80 carbon atoms in the presence of an acid catalyst, wherein the resulting product comprises an alkylated hydroxyaromatic compound having the following structure:

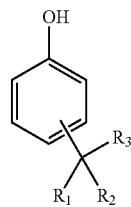

wherein $R_1$ is a branched alkyl group of at least 18 carbon atoms having an average of at least one branch every 2 carbon atoms wherein each branch contains 1 to 2 carbon atoms, $R_2$ is an alkyl group having 1 to 5 carbon atoms, and $R_3$ is either hydrogen or an alkyl group, and further wherein the resulting product is a mixture of ortho and para isomers and wherein the acid catalyst comprises hydrochloric acid, hydrofluoric acid, hydrobromic acid, sulfuric acid, perchloric acid, trifluoromethane sulfonic acid, fluorosulfonic acid, Amberlyst® 36 sulfonic acid or nitric acid.

2. The process according to claim 1, wherein the product comprises from about 1 to 99% ortho isomer and from about 99 to about 1% para isomer.

3. The process according to claim 2, wherein the resulting product comprises from about 5 to about 70% ortho isomer and from about 95 to about 30% para isomer.

4. The process according to claim 1, wherein the branched olefinic propylene oligomer has from about 20 to about 60 carbon atoms.

5. The process according to claim 4, wherein the branched olefinic propylene oligomer has from about 20 to about 40 carbon atoms.

* * * * *